(12) United States Patent
Reid et al.

(10) Patent No.: US 6,599,747 B1
(45) Date of Patent: Jul. 29, 2003

(54) SOIL TEST

(75) Inventors: Brian John Reid, Fife (GB); Kirk Taylor Semple, Lancaster (GB); Kevin Christopher Jones, Lancaster (GB)

(73) Assignee: University of Lancaster, Bailrigg (GB)

( * ) Notice: Subject to any disclaimer, the term of this patent is extended or adjusted under 35 U.S.C. 154(b) by 0 days.

(21) Appl. No.: 09/673,436

(22) PCT Filed: Apr. 16, 1999

(86) PCT No.: PCT/GB99/00973

§ 371 (c)(1),
(2), (4) Date: Jun. 22, 2001

(87) PCT Pub. No.: WO99/54727

PCT Pub. Date: Oct. 28, 1999

(30) Foreign Application Priority Data

Apr. 16, 1998 (GB) .............................................. 9808018

(51) Int. Cl.$^7$ .............................................. G01N 33/24
(52) U.S. Cl. ............................ 436/25; 436/31; 436/60; 436/124; 436/125; 436/126; 436/139; 436/140; 436/141; 436/142; 436/145; 436/177; 436/178
(58) Field of Search .............................. 436/25, 29, 31, 436/60, 124–126, 139–142, 145, 177, 178

(56) References Cited

U.S. PATENT DOCUMENTS 4,444,647 A * 4/1984 Horikoshi et al.

FOREIGN PATENT DOCUMENTS

EP 613735 * 9/1994

OTHER PUBLICATIONS

Wahle, U. et al, Chemosphere 1997, 35, 223–237.*
Loibner, A. P. et al, In Situ and On–Site Bioremedeation, Papers from the International In Situ and On–Site Bioremedeation Symposium 1997, 5, 617–622.*
A. Heitzer et al, Appl. Environ. Microbiol. 1992, 58, 1839–1846.*
A.–S. Allard et al, Appl. Environ. Microbiol. 1994, 60, 777–784.*
J. W. Kelsey et al, Environ. Sci. Tecchnol. 1997, 31, 214–217.*
L. A. Blyshak et al, Anal. Chem. 1988, 60, 2127–2131.*
N. B. Elliott et al, J. Colloid Interface Sci. 1993, 156, 359–364.*
R. S. Brown et al, Anal. Chem. 1996, 68, 287–292.*
A. W. Garrison et al, Environ. Sci. Technol. 1996, 30, 2449–2455.*
E. Fenyvesi et al, Chem. Abstr. 1997, 126, abstract 59360r.*
K. Gruiz et al, Chem. Abstr. 1997, 126, abstract 74275k.*
J. Andreaus et al, J. Colloid Interface Sci. 1997, 185, 306–312.*
M. L. Brusseau et al, Environ. Sci. Technol. 1997, 31, 1087–1092.*
C. A. Groom et al, Electrophoresis 1997, 18, 1166–1172.*
J. Andreaus et al, J. Colloid Interface Sci. 1997, 193, 8–16.*
F. Fava et al, Biotechnol. Bioeng. 1998, 58, 345–355.*

* cited by examiner

*Primary Examiner*—Arlen Soderquist
(74) *Attorney, Agent, or Firm*—Woodard, Emhardt, Moriarty McNett & Henry LLP

(57) ABSTRACT

A test for determining the bioavailable fraction of an organic pollutant present in soil comprises determining the fraction of the organic pollutant present in the soil which may be extracted by a cyclodextrin or derivative thereof.

18 Claims, 1 Drawing Sheet

SOIL TEST

Figure 1:
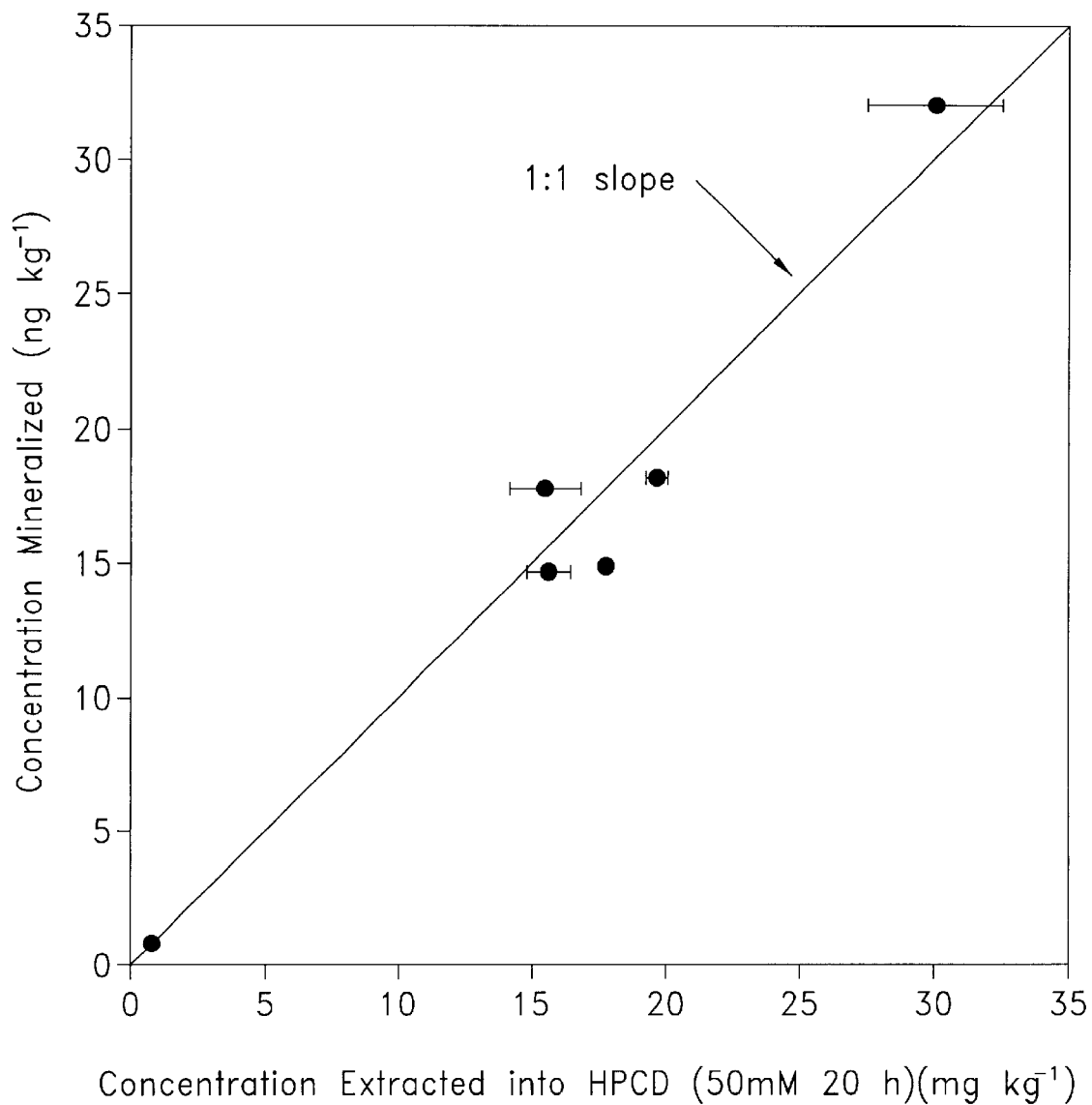

The present invention relates to a test for the analysis of soil, sand, clay and other earth materials (all collectively referred to herein as "soil" for convenience) contaminated with persistent organic pollutants to determine the bioavailable fraction of the pollutant in the soil, particularly but not exclusively for the purposes of deciding whether or not the soil may be purified using a bioremediation strategy.

Various industrial processes may result in contamination of soil with persistent organic pollutants, e.g. polycyclic aromatic hydrocarbons. Examples of industrial processes resulting in such pollution include incineration processes, wood treatment sites, gas works and power stations. It is obviously desirable, for environmental reasons, that such soil be purified. One such strategy for purification is bioremediation in which the soil may be treated by composting, air-sparging or bioaugmentation or by means of a pump and treat procedure or by using a bioreactor so that organisms proliferating in the soil are able to "digest" the pollutants. However the success or otherwise of a bioremediation strategy depends on the bioavailability of the pollutants in the soil. In other words, only a certain fraction (i.e. the bioavailable fraction) of the pollutants in the soil will be removed by the bioremediation strategy. If this fraction is relatively low then the bioremediation technique, whilst reducing the total level of organic pollutants, may not necessary bring the level down below that required by legislation.

The bioavailability of a persistent organic pollutant in soil is dependent on a number of factors. For example, it has been observed that, as the length of time an organic compound remains in contact with soil increases, the ability for that compound to be degraded by micro-organisms decreases (Hatzinger and Alexander, 1995). The rate at which degradation occurs also decreases (Hatzinger and Alexander, 1995). Similarly, a decrease in solvent extractability has been observed as compound/soil contact time increases (Hatzinger and Alexander, 1995; Kelsy et al, 1997). This decrease in compound availability, with time, has been termed "ageing". It is the rapidly desorbed fraction which equates to the bioavailable fraction (Cornelissen 1998).

The nature and extent of ageing is dependent upon soil structure, intra-soil processes and the compound's intrinsic properties. Fundamental parameters include (Brusscau et al. 1991; Jones et al, 1996): aqueous solubility, vapour pressure and octanol: water partition coefficient (Kow). It has been proposed that ageing is the amalgamation of a number of intra-soil process including: sorption onto soil particles (Ball and Roberts, 1991a; Fu et al, 1994; Burgos et al, 1996), diffusion into spatially remote areas such as soil macro and micro pores (Ball and Roberts, 1991b; Beck et al, 1995, Burgos et al. 1996; Pignatello and Xing, 1996) and the entrapment within soil organic matter (Brusseau et al, 1991; Fchen et al; Fu et al, 1994). Neutral organic compounds can interact with the soil through a number of attractive forces, such as, dipole-dipole, dipole-induced dipole and hydrogen bonding (Pignatello and Xing, 1996).

Observation indicates that compound sorption to soil exhibits a biphasic behaviour i.e. following an initial rapid phase of sorption there is a subsequent slower but more prolonged period of sorption (Jones et al, 1996; Pignatello and Xing, 1996). This biphasic behaviour has also been observed in thermal desorption studies (Fu et al, 1994), interestingly sorption/desorption processes have a distinct hysterics, where more compound is sorbed than can subsequently be desorbed (Pignatello, 1991: Fu et al, 1994).

Intra-particle diffusion of compounds into macro- and micro-pores may impede biodegradation on the grounds that pores are of a size small enough to exclude micro-organisms (Chung et al, 1993). Exclusion of micro-organisms on the grounds of size is also postulated to occur where compounds becomes entrapped within large humic macromolecules (Fu et al, 1994). It has been noted that where biodegradation has stopped in the case of aged materials, pulverisation (using a ball mill) of the soil resulted in continued biodegradation (Steinberg et al, 1987). This supports the hypothesis that compounds become trapped within soil micropores as aging proceeds. Investigation (Wu and Gschwend, 1986) into the influence of particle size on the rate of sorption/entrapment, revealed much greater rates of uptake for small particles when compared to large ones.

It is evident that the fate and behaviour of organic compounds within the soil environment is dependent on a complex array of processes. Processes which ultimately govern bioavailability, and thereby dictate the feasibility of bioremediation strategies. At one extreme, where compounds are completely available remediation by a biotechnology should prove favourable. At the other extreme where compounds are recalcitrant in nature, such a strategy may fail, There is a need for a test for the analysis of soil contaminated with persistent organic pollutants to determine whether organic compounds are bioavailable and thereby whether or not a bioremediation strategy will be capable of effecting a sufficient reduction (e.g. to meet legislative requirements) of the amount of pollutants in the soil.

EP-A-0 613 735 discloses a method for the extraction of organic pollutants from contaminated soils. The method involves treatment of the soil with an aqueous solution of a cyclodextrin or derivative thereof. It is stated in this prior specification that cyclodextrins (or their derivatives) enhance the desorption of contaminants from the soil and that this activity can be utilised for the enhancement or the rate of bioremediation of soils contaminated with organic pollutants. As such, the prior specification proposes that the bioremediation of soils contaminated with organic pollutants may be enhanced by treatment of the soil with a cyclodextrin (or derivative thereof) to increase the bioavailability of contaminants to micro-organisms which are capable of degrading the contaminants. However, we have discovered (and this forms the basis of the present invention) that the amount of persistent organic pollutant which a cyclodextrin (or derivative) is able to extract from a soil sample is representative of the amount of the pollutant which is bioavailable and which may therefore be removed by a bioremediation strategy.

On this basis, the present invention provides a test for determining the bioavailable fraction of an organic pollutant present in soil comprising determining the fraction of the organic pollutant present in the soil which may be extracted by a cyclodextrin or derivative thereof.

The present invention is thus to be distinguished from the disclosure in EP-A-0 613 735 in a fundamental way. In the prior specification, the bioremediation strategy is effected by treating the soil inter alia with a cyclodextrin purportedly to increase the bioavailability of the organic pollutant. In contrast, the present invention provides not a bioremediation procedure per se but rather an analysis procedure in which an extraction (of a soil containing persistent organic pollutants) is effected using a cyclodextrin (or derivative thereof) to determine that fraction of the total pollutant which is bioavailable. To a first approximation, the fraction so determined enables a simple calculation to be performed to determine the level of pollutant which would remain in the soil after the bioremediation treatment. Thus it is possible to determine whether the soil is suitable for treatment by bioremediation e.g. to ensure that the remaining pollutant is below legislative maxima.

A preferred test procedure in accordance with the invention comprises the steps of
(a) analysing a first sample of the soil to determine the total amount (or representation thereof) of the organic pollutant which it is desired to remove by a bioremediation strategy,
(b) extracting a sample of the soil with a cyclodextrin (or derivative thereof) to determine the maximum amount (or representation thereof) of the pollutant in this sample which can be extracted by the cyclodextrin (or derivative thereof, and
(c) using the results from (a) and (b) to determine the maximum fraction (or representation thereof) of the total pollutant which can be extracted by the cyclodextrin.

Cyclodextrins as used in the method of the invention are "bucket-shaped" molecules comprising a taurus of α-1, 4linked glucose units, with six units being denoted α-cyclodextrin, seven units being denoted β-cyclodextrin and eight units being denoted γ-cyclodextrin. The procedure of the invention may use α-, β- and/or γ-cyclodextrin. It is also possible to use a cyclodextrin derivative, e.g. an alkylhydroxyalkyl or acyl derivative or any of the other derivatives disclosed in EP-A-0 613 735. It is particularly preferred to use a hydroxy($C_{1-4}$alkyl) derivative most preferably hydroxypropyl-βcyclodextrin (HPCD) which has greater water solubility than β-cyclodextrin.

The method of the invention is applicable particularly, but not exclusively, to pollutants such as polyaromatic hydrocarbons, polychlorinated phenols and biphenyls, dioxines and furanes. If the pollutant is a polyaromatic hydrocarbon having two or three rings then it is preferred that the cyclodextrin is a β-cyclodextrin. If the pollutant is a polyaromatic hydrocarbon with a greater number of rings then it is preferred that the cyclodextrin is a gamma-cyclodextrin.

Cyclodextrin is unstable at a pH below ca5. As such, it should be ensured that extraction procedures utilising cyclodextrin are effected at a higher pH. It is preferred that an unbuffered extraction be used where feasable, i.e. provided that the soil pH is not sufficiently acidic to dissociated the cyclodextrin macromolecule during extraction. Alternatively, although less preferred, a buffered solution may be used to stabilize the cyclodextrin macromolecule. By way of example, the cyclodextrin may be dissolved in:
(i) a buffer comprising $K_2HPO_4$ (0.2 M) and citric acid (0.1 M) in a ratio of 1:1.714 to provide a pH of 6;
(ii) a buffer comprising $K_2HPO_4$ (0.2 M) and $KH_2PO_4$ (0.2 M) in a ratio of 1:0.639 to provide a pH of 7 or in a ratio of 1:0.056 to provide a pH of 8; or
(iii) a buffer comprising $Na_2CO_3$ (0.1 M) and $NaHCO_3$ (0.1 M) in a ratio of 1:9 to provide a pH of 9.2.

The extraction with the cyclodextrin (or derivative thereof) must be such that there is extracted from the soil the maximum amount of pollutant which the cyclodextrin (or derivative) is capable of extracting since otherwise the fraction of bioavailable pollutant in the soil will be underestimated. This will generally imply that the extraction is effected with an excess of the cyclodextrin (or derivative). Thus, it may be necessary to extract two or more soil samples with differing amounts of cyclodextrin (or derivative thereof) to ensure that the maximum amount of pollutant has been extracted. Thus, for example, a series of soil samples may be extracted with progressively increasing amounts of cyclodextrin until a constant amount of pollutant is extracted, this being the maximum amount which may be extracted by means of the cyclodextrin.

Typically the concentration of the cyclodextrin in the solution to be used for extraction of the soil will be in the range 20 mM to 80 mM although we do not preclude values outside this range.

In order to determine whether or not a particular soil sample may be effectively treated using a bioremediation strategy, it is necessary to compare the maximum amount of pollutant which may be extracted by the cyclodextrin with the total amount of pollutant in the soil sample. Various procedures may be used for determining the total amount of pollutants from the soil sample and various possibilities are detailed as (1)–(5) below.

(1) A convenient technique is exhaustive solvent extraction. A solvent extract from the soil may be obtained by a Soxhlet procedure using reflux extraction (cycling solvent vapour through the sample) e.g. for a total of 8–12 hours. The solvent may, for example, be dichloromethane (although this tends to give an extract which is difficult to "clean-up" for the purposes of subsequent analysis), hexane (which is useful if the soil sample is dry since it gives high extraction efficiency and cleaner samples), and a hexane:acetone mix.

(2) A Saponification extraction may be used involving reflux of a mixture of the soil and a saponification lye comprised of 2M KOH mixed with methanol in a ratio 1:4. Reflux may be effected for 6 hours, after which the heat source is removed, the system allowed to cool, and the condensers back washed with fresh saponification lye.

This is a harsher technique than (1) which actively breaks up the soil organic matter thereby releasing very tightly bound compounds.

(3) A sonication technique may be used in which the soil sample to be extracted is mixed with solvent and then placed in a sonicating bath where it is subjected to sonic waves (as an alternative to refluxing in (1) and (2)).

(4) The soil sample to be extracted may be mixed with solvent and then subjected to microwave radiation. This provides a rapid means of obtaining extracts.

The bulk extracts obtained in accordance with procedures (1)–(4) above must generally be concentrated (e.g. by rotary evaporation) to remove excess solvent but not the compounds of interest. The concentrated extracts may then be fractionated to give a clean fraction containing the compounds of interest. Fractionation may most conveniently be achieved by use of chromatographic columns either of a conventional nature, e.g. comprising silica or alumina, or by for example gel permeation chromatography. If necessary, the resultant purified and condensed (?) sample may be reduced in volume again and this may be achieved on a heating block under a stream of nitrogen. The samples are then ready for analysis by, for example, gas chromatography/mass spectrometry or high performance liquid chromatography.

(5) A Super Critical Fluid Extraction may be employed and involves purging the soil sample of interest with liquid carbon dioxide to release the sample compounds of interest. This technique produces clean samples which are virtually ready for analysis but can only be applied to volatile and semi-volatile pollutants.

(6) Volatile organic compounds can also be extracted from soil by a purge and trap method.

It will be appreciated from the above that it can be difficult to determine the actual, absolute total amount of pollutant in the soil and, in fact, different types of pollutants may require different extraction procedures. For this reason, it is convenient to define the maximum amount of a particular pollutant present in a soil by reference to a standard extraction procedure. In accordance with the invention, it is preferred that the procedure for determining the total amount of volatile organic pollutants present in the soil is Method US EPA 8240B as disclosed, for example, in "Guidance Manual on Sampling, Analysis, and Data Management for Contaminated Sites, Volume II: Analytical Method Summaries" as published by the Canadian Council of Ministers of the Environment (the National Contaminated Sites Remediation Program) or is an extraction procedure which is at least as efficient as this procedure. A volatile organic pollutant may be defined as one having a boiling point of less than 200° C. or may be defined by the compound's Henry's Law constant. Volatile organic compounds have relatively high Henry's Law constants, i.e.

$10^3$–$10^5$ Pa m$^3$ mol$^{-1}$ for hydrocarbons

10–$10^5$ Pa m$^3$ mol$^{-1}$ for halogenated hydrocarbons 0.1–100 Pa m$^3$ mol$^{-1}$ for ethers (see Mackay et al. 1993).

For determining the total amount of semi-volatile organic pollutants it is preferred that the procedure is US EPA 8270B as disclosed in the aforementioned reference, or as an extraction procedure which is at least as efficient as this procedure. A semi-volatile organic compound may be defined as one having a boiling point of at least 200° C. or may be alternatively defined as a compound having a LOG octanol-air partition coefficient ($K_{QA}$ greater than 4 where $K_{QA}$ is defined (at equilibrium) as $$K_{OA} = \frac{[Organic\ Pollutant]_{Octanol}}{[Organic\ Pollutant]_{Water}}$$

It must however be appropriate that any one country may have prescribed tests for determining the total amount of persistent organic pollutants present in soil and for any particular to which this patent application extends the term "total amount of pollutant in the soil sample" is to be understood as the amount which can be extracted by the prescribed test.

It will be appreciated from the foregoing description that with the knowledge of (i) the total pollutant content of the soil, and (ii) the maximum pollutant content which may be extracted by the cyclodextrin it is possible to determine for the soil sample the fraction of pollutant which may be removed by a bioremediation strategy. It is thus possible to make a decision as to whether such a strategy would be effected for treating the soil, e.g. to bring the level of pollutants below legislative limits.

Although the present invention has particular application in determining whether or not soil is suitable for a bioremediation strategy, there are other aspects to the invention. In particular, it is possible to use the bioavailable fraction to make a decision as to the degree of hazard (or otherwise) posed by a pollutant in soil. If the bioavailable fraction is relatively low then the pollutant is immobilised and the soil is likely to be "low hazard". Conversely, if the bioavailable fraction is relatively high then the soil may pose a significant hazard.

The invention will be described by way of example only with reference to the following non-limiting Examples and accompanying FIG. 1 of the drawings.

EXAMPLE 1

HPCD Concentration

A sample was "spiked" with 10 mg kg$^{-1}$ $^{14}$C-9phenanthrene. Samples of the soil (1.25 g) were then extracted for 20 hours (sufficient time for extraction of the rapidly i.e. non-kinetically restrained fraction of compounds to be exchanged—see Example 2) with increasing concentration solutions (25 ml) of HPCD in water. The amount of activity exchanged into the HPCD solution was measured as was the total activity present. The results are shown in Table 1 in which the activity units are dpm g$^{-1}$ soil (where dpm stands for disintegrations per minute).

TABLE 1

| HPCD Concentration (mM) | Activity Exchanged into HPCD Solution | Total Activity Present | % Exchangeable with HPCD solution |
| --- | --- | --- | --- |
| 0 | 86.96 | 3116.79 | 2.79 |
| 5 | 1186.25 | 3116.79 | 38.06 |
| 10 | 1429.98 | 3116.79 | 45.88 |
| 20 | 1792.47 | 3116.79 | 57.51 |
| 40 | 2232.56 | 3116.79 | 71.63 |
| 50 | 2005.03 | 3116.79 | 64.33 |
| 60 | 2173.65 | 3116.79 | 69.74 |

These results demonstrate that maximum extraction of the organic pollutant (phenanthrene) was obtained using an HPCD solution having a concentration of 40 mM.

EXAMPLE 2

Extraction Time

The above extraction was repeated but using an HPCD solution having a concentration of 50 mM. However the extraction was terminated after 3, 6, 12, 18, 24 and 40 hours. The results are shown in Table 2 in which the activity units are dpm g$^{31\ 1}$ soil (where dpm stands for disintegration per minute).

TABLE 2

| Extraction Time (h) | Activity Exchanged into HPCD Solution | Total Activity Present | % Exchangeable with HPCD solution |
| --- | --- | --- | --- |
| 0 | 0.0 | 4384.8 | 0.0 |
| 3 | 2813.4 | 4384.8 | 64.2 |
| 6 | 3219.2 | 4384.8 | 73.4 |
| 12 | 3192.1 | 4384.8 | 72.8 |
| 18 | 3264.6 | 4384.8 | 74.5 |
| 24 | 3368.6 | 4384.8 | 76.8 |
| 40 | 3314.9 | 4384.8 | 75.6 |

These results demonstrate that the rapidly i.e. non-kinetically restrained fraction of organic pollutant (phenanthrene) was extracted after an extraction time of 6 h. Thus the use of a 20 h extraction time (Example 1) is valid for assessment.

EXAMPLE 3

Correlation of HPCD Extractability with Biodegradability

Soil was "spiked" to concentrations of 25 and 50 mg kg$^{-1}$. The above extraction was repeated but using a HPCD solution having a concentration of 50 mM. Soil samples were aged for 1, 42 and 84 d prior to extraction. An extraction time of 20 h was used as before (Example 1 and 2 ). The biodegradability of the soil associated $^{14}$C-9-phenanthrene was assessed using respirometry. Respirometers consisted of Erlyn,eyer flasks (250 mL), to which soil (10 g) and water (30 mL) were added. The flasks were innoculated ($10^7$–$10^8$ g$^{-1}$ soil) with a catabolocally active microbial culture. The sealed flasks were shaken and the carbon dioxide evolved from the biodegradation of the phenanthrene trapped in potassium hydroxide (1 M, 1 mL.) Mineralisation was measured until it platcauted (240 h). The results are shown in Table 3 and FIG. 1.

| Ageing time (d) | Original "Spiked" Phenanthrene Concentration (mg/kg$^{-1}$) | Concentration Extracted into HPCD Solution (mg/kg$^{-1}$) | Concentration Mineralized by microbes (mg/kg$^{-1}$) |
|---|---|---|---|
| 1 | 25 | 19.5 | 18.2 |
| 42 | 25 | 17.6 | 14.9 |
| 84 | 25 | 15.5 | 14.7 |
| 1 | 50 | 29.9 | 32.0 |
| 42 | 50 | 15.4 | 17.8 |
| 84 | 50 | 1.0 | 1.1 |

The results indicate that the extraction of soil associated phenanthene by an aqueous HPCD solution as described above provides good correlation (slope=1.041; $1^{0.2}$=0.980) with the amount of phenanthrene which can be biodegraded by catabolically active microorganisms. Furthermore prediction can be made over a range of concentrations and after a range of ageing times.

REFERENCES

Ball, W. P., And Roberts. P. V. 1991a. Long term sorption of halogenated organic chemicals by aquifer material. I. Equilibrium. Environ. Sci. Technol. 25, 1223–1235.

Ball. W. P., and Roberts, P. V. 1991b. Long term sorption of halogenated organic chemicals by aquifier material. 2. Intraparticle diffusion. Environ. Sci. Technol. 25, 1237–121249.

Beck, A. J. Wilson, S. C., Alcock, R. E., and Jones, K. C. 1995. Kinetic constraints on the remediation of soils contaminated with organic chemicals: implications for soil quality limits. Crit. Rev. Environ. Sci. Technol. 25, 1–43.

Rosma, T. N. P. . Middeldorp, P. J. M., Schraa, G., and Zehnder, J. J. B. 1997. Mass transfer limitations of biotransformation: Quantifying Bioavailability, Env. Sci. Technol. 31, 248–252.

Brusseau. M. L., Jessup, R. E., and Rao, P. S. C. 1991. Nonequilibrium sorption of organic chemicals:elucidation of rate limiting processes. Env. Sci. Technol. 25. 134–142.

Burgos, W. D., Novak, J. T., and Berry, D. F. 1996. Reversible sorption and irreversible binding of naphtldalence and α-naphthol to soil:elucidation of processes. Env. Sci. Technol. 30, 1205–1211.

Chen, Z., Xing, B., M$^c$Gill W. B., and Dudas, M. J. 1996. α-Naphthol sorption as regulated by structure and composition of organic substances in soil and sediment. Can. J. Soil. Sci. 76, 513–522.

Chung, A-Y. M$^c$Coy, B. J., and Scow, K. M. 1993. Criteria to assess when biodegradation is kinetically limited by intraparticle diffusion and sorption. Biotech. Bioeng. 41, 625–632.

Cornellisen, G., Rigterink, H., Ferdinandy, H. M. A., and VanNoort, P. C. M. 1998. Rapidly desorbing fractions of PAHs in contaminated sediments as a predictor of extent of bioremediation. Environ. Sci. Technol. 32, 966–970.

EPA/540/S5-91/009, 1993. Pilot-scale demonstration of a slurry-phase biological reactor for creosote-contaminated soil.

Fu, G., Kan, A. T., and Tomson, M. 1994. Adsorption and desorption hysteresis of PAHs in surface sediments. Environ. Toxicol. Chem. 13, 1559–1567.

Guerin, W. F., and Boyd, S. A. 1992. Differential bioavailability of soil sorbed naphthalene to two bacterial species. Appl. Env. Microbiol. 58, 1142–1152.

Hatzinger. P. B., and Alexander, M. 1995 Effect of Aging of chemicals in Soil on Their Biodegradability and Extractability. Env. Sci. Technol. 29, 537–545.

Jones, K. C., Alcock;, R. E., Johnson, D. L., Northcott, G. L., Semple, K. T., and Woolgar, P. J. 1996. Organic Chemicals in Contaminated Land: Analysis, Significance and Research Priorities, Land. Contam. Reclam. 4, 189–197.

Kelsey, J. W., Kottler, B. D., and Alexander, M. 1997. Selectiv Chemical Extractants to Predict Bioavaibility of Soil-Aged Organic Chemicals. Env. Sci. Technol. 31, 214–217.

Loehr, R. C., and Webster, M. T. 1997. Changes in toxicity and mobility resulting from bioremediation processes. Bioremediation Journal. 1, 149–163.

Mackay, D., Shiu, W. Y., and Ma, K. C., Illustrated Handbook of Physical-Chemical Properties and Environmental Fate of Organic Chemicals, Volume III Volatile Organic Chemicals, 1993.

May, R., Shroder, P., and Sandmann, H, 1997. ExSitu processes for the treating PAH-contaminated soil with *Phanerochaete chrysporium*. Env. Sci. Technol. 31,2626–2633.

Pignatello, J. J. 1991. Desorption of tetrachloroethene and 1,2-dibromo-3-chloropropane from aquifer sediments. Environ. Toxicol. Chem. 10. 1399–1404.

Pignatello, J. J., and Xing, B. 1996. Mechanisms of slow sorption of organic chemicals to natural particles. Env. Sci. Technol. 30, 1–11.

Smith. J. R., Tomicek, R. M., Swallow, P. V., Weightman, R. L., Nakes, D. V, and Helbling, M. 1995. Hydrocarbon contaminated soils. Vol. V. Eds. 79–83. Kustecki et al. Amerherst Scientific Publishers.

Steinbert, S. M., Pignatello, J. J., and Sawhney, B. L. 1987. Persistence of 1,2-dibromoethane in soils: entrapment in intraparticle micropores. Environ. Sci. Technol. 21, 1237–1208.

Subba-Rao, R. V., and Alexander, M. 1982. Effect of sorption on mineralisation of low concentrations of aromatic compounds in lake water samples. Appln. Env. Microbiol. 44, 659–68.

Van der Meer. J. R., 1994. Potenitial and limitations to the use of microbiological methods for the treatment of environmental pollution. EAWAG News. 36, 20–24.

Wu, S. C., and Gschwend P. M. 1986. Sorption kinetics of hydrophobic organic compounds to natural sediments and soils. Environ. Sci. Technol. 20, 717–725.

What is claimed is:

1. A test for determining a bioavailable fraction of an organic pollutant present in soil comprising determining a total amount of an organic pollutant in the soil and determining a maximum fraction of the organic pollutant present in the soil which may be extracted by a solution of a cyclodextrin or derivative thereof.

2. A test as claimed in claim 1 comprising the steps of
   (a) analyzing a sample of the soil to determine a total amount, or representation thereof, of the organic pollutant which can be extracted from the soil sample,
   (b) extracting a sample of the soil with a solution of a cyclodextrin, or derivative thereof, to determine a maximum amount, or representation thereof, of the pollutant in this sample which can be extracted by the cyclodextrin, or derivative thereof, and
   (c) using the results from (a) and (b) to determine the maximum fraction, or representation thereof, of the total pollutant which can be extracted by the cyclodextrin.

3. A test as claimed in claim 2 wherein for a volatile organic pollutant the total amount of that pollutant in the soil is determined in accordance with US EPA 8240B or a procedure which provides at least the same value of the total amount.

4. A test as claimed in claim 2 wherein for a semi-volatile organic pollutant the total amount of that pollutant in the soil is determined in accordance with US EPA 8270B or a procedure which provides at least the same value of the total amount.

5. A test as claimed in claim 1 wherein the extraction with the cyclodextrin or derivative thereof is effected using an unbuffered aqueous solution of the cyclodextrin or derivative thereof under conditions preventing dissociation of the cyclodextrin.

6. A test as claimed in claim 1 wherein the extraction with the cyclodextrin or derivative thereof is effected using a buffered solution.

7. A test as claimed in claim 6 wherein the buffer comprises $H_2PO_4$ ion containing salts and citric acid.

8. A test as claimed in claim 7 wherein the salt is selected from the group consisting of the potassium salt and the sodium salt.

9. A test as claimed in claim 6 wherein the buffer comprises $HPO4^{2-}$ and $H_2PO_4^-$ ion containing salts.

10. A test as claimed in claim 9 wherein the salt is selected from the group consisting of the potassium salt and sodium salt.

11. A test as claimed in claim 6 wherein the buffer comprises $CO_3^{2-}$ and $HCO_3^-$ ion containing salts.

12. A test as claimed in claim 11 wherein the salt is selected from the group consisting of the potassium salt and the sodium salt.

13. A test as claimed in claim 1 wherein the cyclodextrin or derivative thereof is used as a solution having a concentration of 20 mM to 80 mM.

14. A test as claimed in claim 1 wherein the extraction with the cyclodextrin or derivative thereof is effected with a hydroxy($C_{1-4}$ alkyl) cyclodextrin derivative.

15. A test as claimed in claim 14 wherein the derivative is hydroxypropyl-β-cyclodextrin.

16. A test as claimed in claim 1 wherein the total amount of the organic pollutant is determined using exhaustive solvent extraction.

17. A method for determining whether or not a soil contaminated with organic pollutants is suitable for purification by a bioremediation strategy, the test comprising the steps of
  (i) determining the bioavailable fraction of the organic pollutants in accordance with the test procedure of claim 1, and
  (ii) using the fraction from (i) to make a decision as to whether or not the soil is suitable for bioremediation.

18. A method for determining soil hazard comprising the steps of
  (i) determining the bioavailable fraction of the organic pollutants in accordance with the test procedure of claim 1, and
  (ii) using the fraction from (i) to make a decision as to the hazard posed by the soil.

* * * * *